(12) United States Patent
Potyrailo et al.

(10) Patent No.: US 6,683,689 B2
(45) Date of Patent: Jan. 27, 2004

(54) METHOD FOR RAPID DETERMINATION OF COMPOSITION OF POLYCARBONATE RESIN

(75) Inventors: Radislav Alexandrovich Potyrailo, Niskayuna, NY (US); Patrick Joseph McCloskey, Watervliet, NY (US)

(73) Assignee: General Electric Company, Niskayuna, NY (US)

( * ) Notice: Subject to any disclaimer, the term of this patent is extended or adjusted under 35 U.S.C. 154(b) by 184 days.

(21) Appl. No.: 09/682,654

(22) Filed: Oct. 2, 2001

(65) Prior Publication Data

US 2003/0063282 A1 Apr. 3, 2003

(51) Int. Cl.[7] .................. G01N 21/00; G01J 5/02; G01T 1/20
(52) U.S. Cl. ............... 356/432; 356/433; 356/440; 250/339.12; 250/343; 250/365
(58) Field of Search ................ 356/432, 433, 356/436, 440; 250/339.12, 343, 365

(56) References Cited

U.S. PATENT DOCUMENTS

| | | | |
|---|---|---|---|
| 4,907,883 A | 3/1990 | Allmon et al. | 356/317 |
| 5,151,491 A | 9/1992 | Sakashita et al. | 528/199 |
| 5,550,630 A | 8/1996 | Chrastil | 356/300 |
| 5,574,232 A | 11/1996 | Davidson et al. | 73/864.81 |
| 6,166,133 A | 12/2000 | Catsman | 525/67 |
| 6,184,334 B1 | 2/2001 | McCloskey et al. | 528/196 |
| 6,193,850 B1 * | 2/2001 | Potyrailo et al. | 204/157.15 |
| 6,252,035 B1 | 6/2001 | McCloskey et al. | 528/196 |
| 6,544,795 B1 * | 4/2003 | Carnahan | 436/128 |
| 6,552,787 B1 * | 4/2003 | Potyrailo et al. | 356/317 |

FOREIGN PATENT DOCUMENTS

EP 0 985 696 A1 3/2000

OTHER PUBLICATIONS

Blair, D.S., et al., *Anal Chem.*, 69:2238–2246 (1997).
Chalmers, J.M., Everall, N.J., *Trends Anal. Chem.*, 15:18–25 (1996).
Everall, N.J. et al., *Appl. Spectrosc.* 49:610–615 (1995).
H. Mark, and J. Workman, *Statistics in Spectroscopy*: Academic Press: San Diego, CA, pp. 263–276 (1991).
Ingle, J.D., Jr., Crouch, S.R., *Spectrochemical Analysis*, Prentice Hall: Englewood Cliffs, N.J. (1988).
Miller, J.C., Miller, J. N., *Statistics for Analytical Chemistry*, Ellis Horwood, New York, NY, pp. 101–139 (1993).
Mork, C. O., Priddy, D. B, *J. Appl. Polym. Sci.*, 45:435–442 (1992).
Robertson, G., *Appl. Spectrosc.*, 55:98–104 (2001).
Shchori, E., McGrath, J.E., *J. Appl. Polym. Sci., Appl. Polym. Symp.*, 34:103–117 (1978).

* cited by examiner

Primary Examiner—Russell Adams
Assistant Examiner—Magda Cruz
(74) Attorney, Agent, or Firm—Andrew J. Caruso; Patrick K. Patnode

(57) ABSTRACT

The invention comprises UV/visible spectroscopic analysis of polycarbonate composition. The method comprises determination of the concentration of Fries products, as either total Fries products or as separate determinations of linear and branched components. The method also allows for simultaneous determination of uncapped phenolic endgroups. Determinations may be performed at a single wavelength or over the entire absorption band. The method is suitable for measuring of Fries products in samples ranging in size from small scale combinatorial formats to production scale reactors. The method is independent of reaction variables such as polymer molecular weight, reactor type, and reaction temperature.

41 Claims, 15 Drawing Sheets

METHOD FOR RAPID DETERMINATION OF COMPOSITION OF POLYCARBONATE RESIN

BACKGROUND OF INVENTION

The invention relates to the rapid and noninvasive measurement of polycarbonate composition. In particular, the method describes determination of the concentration of total Fries rearrangement products, or their separate linear and branched components, as well as uncapped phenolic end-groups, by a combination of UV/visible absorbance spectroscopy and multivariate data analysis.

The melt (LX) polymerization process utilizing bisphenol A (BPA) and diphenyl carbonate (DPC) is one of the most efficient non-phosgene routes of polycarbonate production. Still, the formation of Fries rearrangement products during melt polymerization can be problematic. Fries rearrangement products result from the conversion of phenolic esters into corresponding ortho and para hydroxyketones as a result of the inherent stability of polybenzenoid compounds. Polycarbonates produced by the melt process typically have higher Fries content than polycarbonates produced by the interfacial method. Excess Fries product can lead to differences in physical properties, such as flow and ductility, between polycarbonate produced by the melt process and polycarbonate produced by more traditional interfacial methods. It is important, therefore, to monitor and control for excess Fries produced during polymerization. In addition, in many cases it is also important to monitor the amount of "uncapped" polymer chains. Uncapped polymer chains are those chains which terminate in a free phenolic group, as opposed to being terminated with an aryl carbonyl group. It has been found that the hydrolytic stability of polycarbonate is inversely proportional to the amount of uncapped chain ends. Thus, a method which provides accurate analysis of Fries products and the amount of uncapped chain ends would be of value for the optimization of polymerization reaction conditions, both in the research setting and for on-line monitoring at the production scale.

Conventional techniques for monitoring Fries products generally involve analyzing aliquots from the reaction mixture by methods such as liquid chromatography (LC), or nuclear magnetic resonance (NMR). Similarly, techniques employed for the analysis of phenolic end-groups include IR spectroscopy, proton NMR, and potentiometric titration. These and other known methods of laboratory analysis, however, are time consuming and/or require relatively large sample sizes. Furthermore, these methods are not well-suited to on-line analysis of polycarbonate formed during large-scale production in that they require multiple sample preparation steps which are time-consuming, add to the overall error, are potentially dangerous at the high temperatures used for polymerization, and are not easily adaptable for remote monitoring using optical fibers. Also, removing aliquots may alter the reaction conditions or sample constitution, and provides only temporally discrete data points, rather than a continuous profile.

As an alternative to monitoring reactions during the polymerization, samples may be analyzed after the reaction is complete, and unsatisfactory products discarded. For example, a known technique for monitoring phenolic end-groups employs ultraviolet (UV) absorption spectroscopy to measure absorbance of phenolic end-groups at about 287 nm. Another technique for monitoring phenolic end-groups employs ratiometric ultraviolet absorption spectroscopy where absorbance of carbonate units in the spectral region of about 266 or 272 nm is compared to the absorbance of phenolic end-groups at about 287 nm. The measurements are typically performed by dissolving the polymer in a suitable solvent followed by UV spectrophotometric analysis or by a gel permeation chromatography and UV analysis (E. Shchori and J. E. McGrath, J. Appl. Polym. Sci., Appl. Polym. Symp., 34:103–117 (1978); and C. O. Mork and D. B. Priddy, J. Appl. Polym. Sci., 45:435–442 (1992). Post-reaction sampling, however, does not enable real-time optimization of reaction parameters and, therefore, may result in the synthesis of a polymer batch of substantially inferior quality.

Thus, there is a need for noninvasive methods for monitoring levels of linear and branched Fries rearrangement products and phenolic end-groups for polycarbonate synthesis reactions. Reaction monitoring should be independent of reaction variables unrelated to the reaction component of interest, such as the starting materials and catalysts used, as well as reaction parameters such as final polymerization temperature, reactor design, and product molecular weight. As there is a continuing need to evaluate economically superior reactant systems, the method should be adaptable to combinatorial (small-scale) evaluation of new reactant and catalyst combinations, as well as on line monitoring of large-scale production systems.

SUMMARY OF INVENTION

The present invention is directed to a method for monitoring polymerization reactions and reaction components using electronic absorbance spectroscopy. The invention provides methods for the analysis of linear and branched chain Fries products and phenolic end-groups formed during polymer synthesis, as for example, during the production of polycarbonate by melt polymerization. The methods of the present invention are non-invasive, and suitable for small-scale combinatorial formats as well as large-scale production monitoring.

Thus, in one aspect, the invention comprises a method for monitoring polymer composition comprising irradiating a sample comprising at least one polymer and/or oligomer with at least one substantially monochromatic radiation, monitoring UV/visible light absorbed by the irradiated sample, and correlating the light absorbed by the irradiated sample to at least one pre-determined reaction component, wherein one of the predetermined reaction components comprises Fries products.

In another aspect, the present invention comprises a method for monitoring polycarbonate composition comprising irradiating a polycarbonate sample comprising polymer and/or oligomer with at least two wavelengths of substantially monochromatic radiation, monitoring UV/visible light absorbed by the irradiated polycarbonate, and correlating the light absorbed by the irradiated polycarbonate to Fries products and un-capped phenolic end-groups in the irradiated polycarbonate.

BRIEF DESCRIPTION OF DRAWINGS

Various features, aspects and advantages of the present invention will become more apparent with reference to the following description, appended claims, and accompanying drawings, wherein:

DETAILED DESCRIPTION

Figure 1:
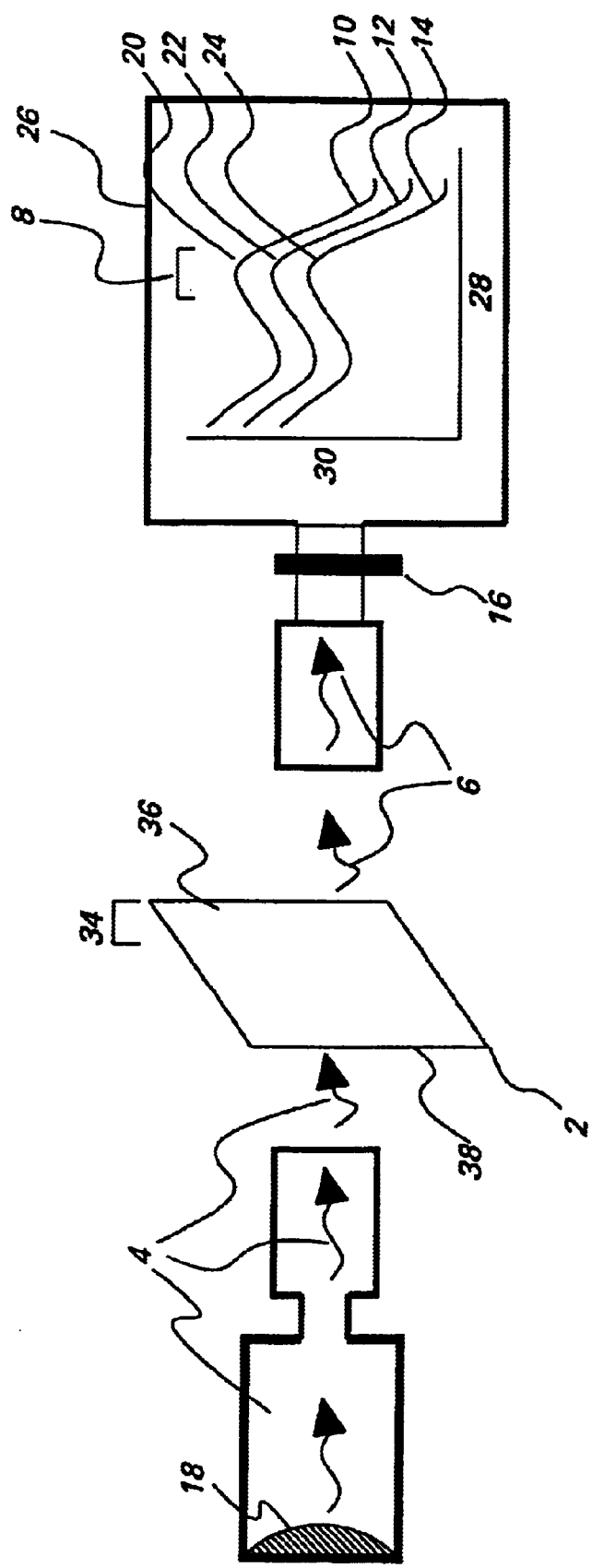
FIG. 1 is a representation of an aspect of an embodiment of the method of the invention.

Terms used herein are employed in their accepted sense or are defined. The present invention is directed to noninvasive methods for measuring total Fries products, where total Fries products comprises both linear and branched Fries products, or for independent quantification of linear and branched chain Fries in a sample. The sample may comprise polymer, oligomer, or polymer and oligomer mix. Preferably, the sample comprises melt polycarbonate formed by polymerization of bisphenol A (BPA) and diphenyl carbonate (DPC). The present invention is also directed to noninvasive methods for measuring uncapped polymer end chains, where uncapped polymer end chains comprise phenolic end-groups. More specifically, the present invention relates determination of Fries rearrangement products and uncapped end-groups by UV/visible absorption spectroscopy by multivariate analysis. The methods of the present invention may be adapted for on-line monitoring in a production scale setting, or for the analysis of multiple small-scale reactions, as for example, in a combinatorial library. The methods of the present invention are not sensitive to reaction temperature, catalyst type, final polymer molecular weight, or reactor design.

In one aspect, the invention comprises a method for monitoring sample polymer composition comprising irradiating a sample comprising at least one polymer and/or oligomer with at least one substantially monochromatic radiation, monitoring UV/visible light absorbed by the irradiated sample, and correlating the light absorbed by the irradiated sample to at least one pre-determined reaction component, wherein one of the predetermined reaction components comprises Fries products.

Preferably, the sample comprises polycarbonate. More preferably, the sample comprises melt polycarbonate produced by polymerization of bisphenol A (BPA) and diphenyl carbonate (DPC).

In an embodiment, the Fries rearrangement products comprise linear and branched chain Fries products. Alternatively, the method may consist of quantification of linear Fries products. In another embodiment, the method may consist of quantification of branched Fries products.

For analysis of sample Fries, the monitored absorbance preferably comprises at least one monochromatic wavelength in the range of 250 to 450 nm. More preferably, the monitored absorbance comprises at least one substantially monochromatic wavelength in the range of 280 to 400 nm. Even more preferably, the monitored absorbance comprises at least one substantially monochromatic wavelength in the range of 290 to 330 nm. Even more preferably, the monitored absorbance comprises a wavelength of about 320 nm.

The method of the present invention may utilize univariate analysis for quantitative prediction of the level of Fries products. Alternatively, the invention may comprise monitoring the absorbed light at more than one wavelength. Thus, the method may comprise multivariate analysis.

In an embodiment, the method includes correlating the light absorbed by the irradiated sample to a second predetermined reaction component. Preferably, the second predetermined reaction component comprises uncapped phenolic end-groups. For analysis of sample Fries and uncapped end-groups, the monitored absorbance preferably comprises at least two substantially monochromatic wavelengths in the range of 250 to 450 nm. More preferably, the monitored absorbance comprises at least two substantially monochromatic wavelengths in the range of 260 to 400 nm. Even more preferably, the monitored absorbance comprises at least two substantially monochromatic wavelengths in the range of 270 to 340 nm.

In an embodiment, irradiation and collection of absorbed light is performed on solid polycarbonate. In yet another embodiment, irradiation and collection of absorbed light may be performed on dissolved polycarbonate.

Preferably, the monitored absorbance is insensitive to the presence of fluorescent species in the sample. Also preferably, the monitored absorbance is insensitive to the molecular weight of the sample. The monitored absorbance is also preferably insensitive to the reaction temperature used to generate the sample. The monitored absorbance is also preferably insensitive to the reactor type used to generate the sample. In another aspect, the present invention comprises a method for monitoring polycarbonate composition comprising irradiating a polycarbonate sample comprising polymer and/or oligomer with at least two wavelengths of substantially monochromatic radiation, monitoring UV/visible light absorbed by the irradiated polycarbonate, and correlating the light absorbed by the irradiated polycarbonate to Fries products and un-capped phenolic end-groups in the irradiated polycarbonate. Preferably, the polycarbonate comprises melt polycarbonate produced by polymerization of bisphenol A (BPA) and diphenyl carbonate (DPC).

In an embodiment, the Fries rearrangement products comprise linear and branched chain Fries products. Alternatively, the method may consist of quantification of linear Fries products. In another embodiment, the method may consist of quantification of branched Fries products.

For analysis of sample Fries and uncapped end-groups in melt polycarbonate, the monitored absorbance preferably comprises at least two monochromatic wavelengths in the range of 250 to 450 nm. More preferably, the monitored absorbance comprises at least two monochromatic wavelengths in the range of 260 to 400 nm. Even more preferably, the monitored absorbance comprises at least two monochromatic wavelengths in the range of 270 to 340 nm.

Preferably, the monitored absorbance is insensitive to the presence of fluorescent species in the sample. Also preferably, the monitored absorbance is insensitive to the molecular weight of the sample. The monitored absorbance is also preferably insensitive to the reaction temperature used to generate the sample. Also, the monitored absorbance is preferably insensitive to the reactor type used to generate the sample. The invention further comprises computer readable media comprising software code for performing the methods of the invention.

In another aspect, the present invention comprises a method for monitoring polycarbonate composition comprising irradiating a polycarbonate sample comprising at least one polymer and/or one oligomer with one substantially monochromatic radiation, monitoring UV/visible light transmitted by the irradiated sample, and correlating the light absorbed by the irradiated sample to levels of Fries products.

In another aspect, the invention comprises a method for monitoring polycarbonate composition comprising irradiating a polycarbonate sample comprising at least one polymer and/or one oligomer with at least two wavelengths of substantially monochromatic radiation, monitoring UV/visible light transmitted by the irradiated sample, and correlating the light absorbed by the irradiated sample to levels of linear Fries and branched Fries products in the sample.

In yet another aspect, the invention comprises a method for monitoring polycarbonate composition comprising irradiating a polycarbonate sample comprising at least one polymer and/or one oligomer with at least three wavelengths of substantially monochromatic radiation, monitoring UV/visible light transmitted by the irradiated sample; and correlating the light absorbed by the irradiated polymer to levels of linear Fries and branched Fries products and phenolic end-groups in the sample.

Thus, the invention describes using absorbance spectroscopy for measuring linear and branched Fries rearrangement products as well as phenolic end-groups present in polycarbonate samples. The polycarbonate may comprise oligomers, polymers, or a mix of oligomers and polymers. Because the method is non-invasive, and employs a simple format, it can be adapted for both large-scale production monitoring of polymer formation, as well as small scale combinatorial development of new reaction conditions and catalysts.

The invention describes the use of UV/visible absorbance spectroscopy to monitor the composition of samples comprising at least one polymer and/or oligomer. When radiation passes through a transparent layer of solid, liquid or gas, certain frequencies of radiation may be selectively removed by absorption. As defined herein, absorption of radiation occurs when electromagnetic energy is transferred to the atoms or molecules of the sample and these particles are promoted from a low energy (ground) state to higher energy, or excited states. Because atoms and molecules have a limited number of discrete, quantified energy levels, for absorption of radiation to occur, the energy of the exciting photon must match the energy difference between the ground state and one of the excited states of the absorbing species.

As defined herein, polycarbonate comprises long-chain linear polyesters of carbonic acid and dihydric phenols, such as bisphenol A (BPA). Generally, polycarbonate is produced either by interfacial polymerization or transesterification. In interfacial polymerization, BPA is phosgenated in an aqueous solution of sodium bisphenolate with methylene chloride as an organic solvent. Melt polycarbonate comprises polycarbonate formed by the transesterification process in which BPA reacts with diphenyl carbonate (DPC) in a molten state without the solvent (see e.g. J. A. King, Synthesis of Polycarbonates, In Handbook of Polycarbonate Science and Technology, eds. D. G. LeGrand and J. T. Bender; Marcel Dekker, Inc., N.Y.). Generally, polymers are defined as compounds of greater than 7500 number average molecular weight (Mn) and oligomers are compounds comprising more than one subunit, but less than 7500 Mn.

Fries rearrangement products result from the conversion of phenolic esters into corresponding ortho and para hydroxyketones as a result of the inherent stability of polybenzenoid compounds. Fries products in melt polycarbonate generally include compounds having the following repeating unit:

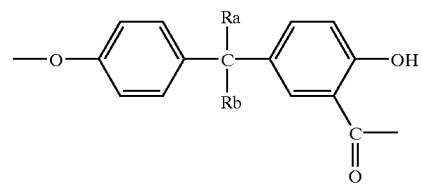

wherein variables $R_a$ and $R_b$ each independently represent a hydrogen atom or a monovalent hydrocarbon group and may form a ring structure. In some instances, it is advantageous to know the amount of linear or branched Fries products, rather than just total Fries. Linear Fries products in melt polycarbonate generally include compounds having the following structure:

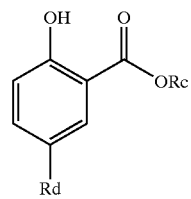

and branched Fries products in melt polycarbonate generally include compounds having the following structure:

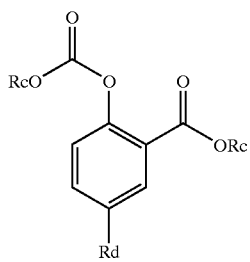

where $R_c$=bisphenol A, and $R_d$=isopropylidine(-4-phenol) in oligomeric and polymeric polycarbonate, and $R_c$=phenyl, and $R_d$=a hydrogen atom in standard (model) materials.

In an embodiment, the invention comprises methods to measure uncapped phenolic end-groups in polycarbonate. As defined herein, uncapped polymer chains are those chains which terminate in a free phenolic group, as opposed to being terminated with an aryl carbonyl group.

Referring now to FIG. 1, the invention comprises a method for monitoring sample composition comprising the steps of irradiating at least one sample 2 with a substantially monochromatic radiation 4, collecting light transmitted 6 from the irradiated sample 2, monitoring at least one wavelength 28 corresponding to absorbed light 30, and correlating the change in at least one wavelength 28 of the collected spectrum to Fries product and/or phenolic end-groups in sample 2. Substantially monochromatic light generally comprises radiation having a very narrow band of wavelengths, such that the variation is about 1 nm. For example, whereas sample 2 may have absorbance spectrum 10 with an absorbance value of 20 at spectral region 8, other samples having different levels of Fries products have absorbance spectra 12 and 14 with difference levels of absorbance 22 and 24, respectfully, at spectral region 8 corresponding to Fries absorbance. Preferably, absorbance 30 at spectral region 8 is independent of the presence of fluorescent or light scattering species in the sample.

Absorbance may be measured using a desktop diode array spectrometer comprising a Xe arc lamp, a deuterium lamp, a tungsten-halogen lamp, and combinations thereof. Generally, the lamp emission level and detector sensitivity are controlled so that the detector of the spectrometer is not saturated. For example, an in-line short-pass filter 16 may be positioned between the light source 18 and the spectrometer 26. Preferably, samples are of about equal thickness, with measurements either at, or close to, a defined absorption band.

In an embodiment, sample 2 contains at least one polymer and/or oligomer. In an embodiment, sample 2 is melt polycarbonate. For example, Fries levels in production stage polycarbonate, such as materials from oligomerization stage or polymerization stage melt polycarbonate, may be measured by the method of the invention. Irradiation and collection of absorbance spectra may be performed on combinatorial libraries of samples dispersed in a 96-well microtiter plate reactor or other type of array. The method may be used to measure melt polycarbonate generated in a small scale batch reactor as well as in a continuous system.

The absorbance spectrum may be monitored at one wavelength for univariate analysis, or at more than one wavelength for multivariate analysis. In an embodiment, the absorbance characteristics of the sample are analyzed using statistical techniques. For example, the absorbance characteristics of the sample may be analyzed using univariate linear regression calibration methods (see e.g. H. Mark and J. Workman, Statistics in Spectroscopy: Academic Press: San Diego, Calif., pp. 263–276 (1991); and J. C. Miller and J. N. Miller, Statistics for Analytical Chemistry, Ellis Horwood, New York, N.Y., pp. 101–139 (1993)). Univariate calibration models may be derived which provide quantitative prediction of Fries products in a sample based on absorbance measurements at one wavelength. Alternatively, univariate calibration models may be derived which provide quantitative prediction of linear Fries products, or branched Fries products, or uncapped end-groups, in a sample based on absorbance measurements at one wavelength.

Figure 2:
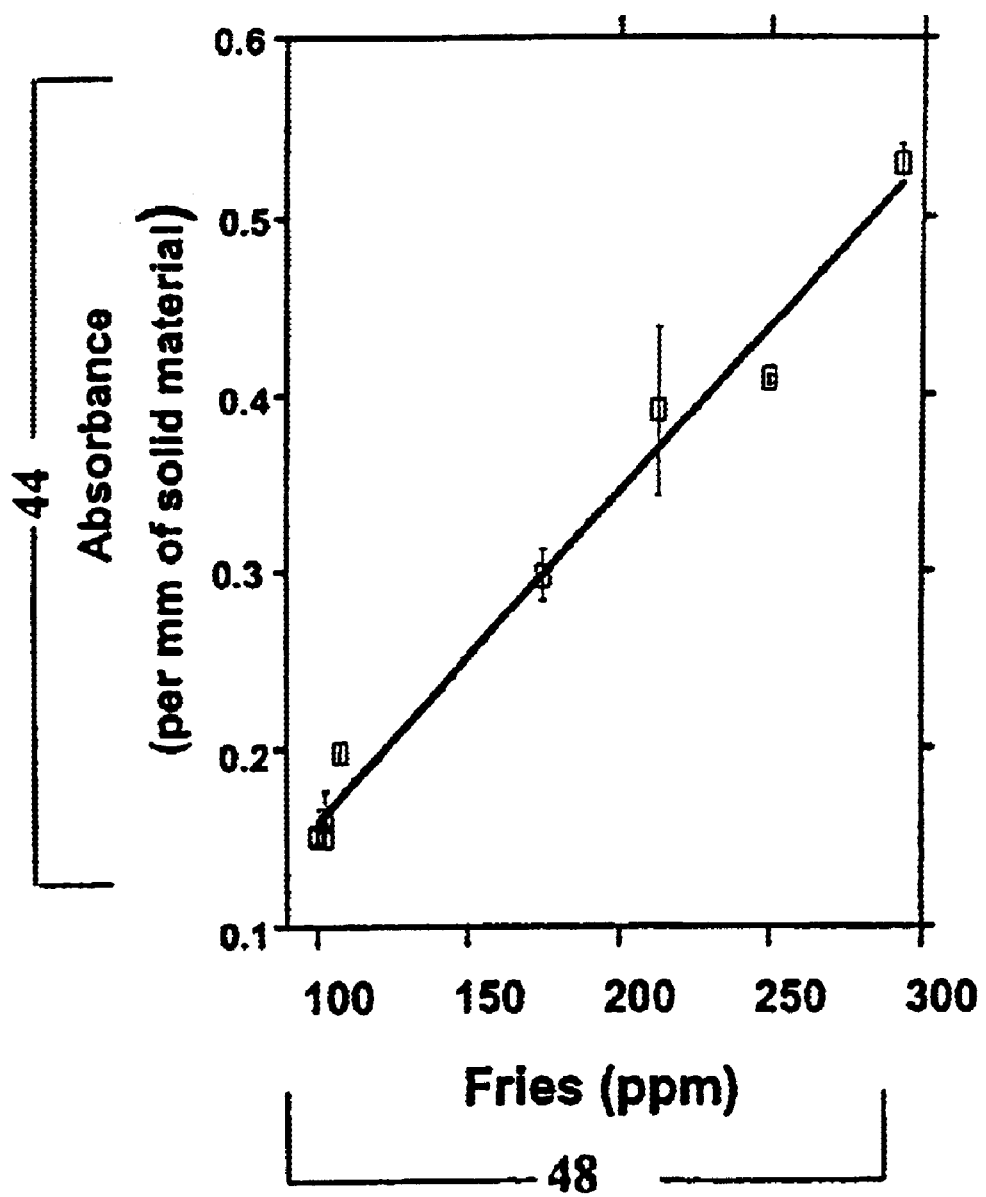
FIG. 2 illustrates an aspect of an embodiment of the invention comprising UV/visible absorption measurements at 320 nm of Fries product in solid melt polycarbonate using a diode array spectrophotometer wherein the calibration curve is derived from the absorption spectra and error bars are one standard deviation (SD) from the mean (n=3).

Preferably, samples comprising differing amounts of Fries comprise distinct absorbance values at a specifically identified wavelength range. Referring now to FIG. 2, it can be seen that for solid polycarbonate, the absorbance 44 increases at 320 nm as a function of sample Fries products 48. Measurements may be made using either a desktop diode array spectrophotometer (e.g. for analysis of combinatorial arrays) (FIG. 2) or using any other UV/visible spectrophotometer. Because light transmittance through a sample is dependent upon the thickness 34 of the sample, solid sample 2 should have surfaces 36 and 38 which are reasonably parallel (FIG. 1). Preferably, sample 2 is thin enough for absorbance measurements, but thick enough for routine manipulation. Polycarbonate samples that are about 1 to about 4 mm thick and which vary less than 0.2 mm in thickness have been found to be suitable for quantification of Fries products by the method of the invention.

Figure 3:
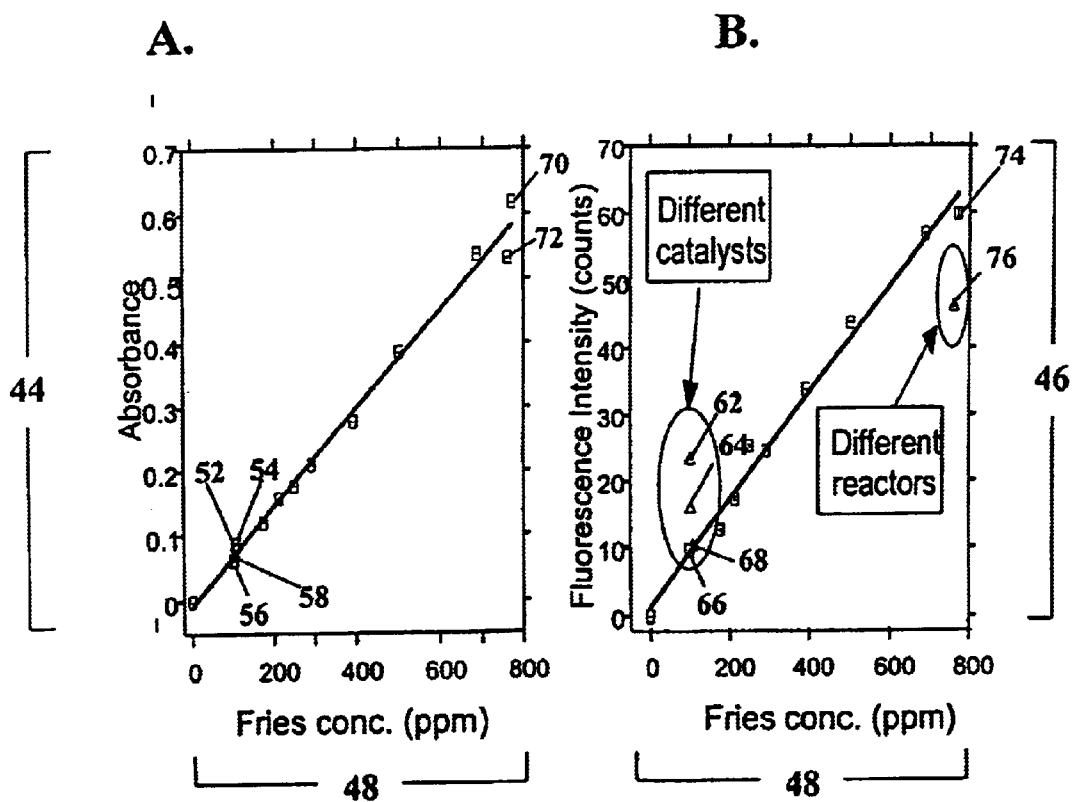
FIG. 3 illustrates an aspect of an embodiment of the invention comprising measurements of Fries product in dissolved oligomer material, wherein error bars are one SD from the mean (n=3) and (A) is absorbance at 320 nm and (B) is fluorescence at 500 nm.

Alternatively, the sample may also be dissolved in a solvent. For example, melt polycarbonate can be dissolved in organic solvents such as chloroform, tetrahydrofuran, dichloromethane, and the like. Analyzing polycarbonate in liquid form reduces the effect of sample inhomogeneities found in solid polycarbonate, and avoids having to generate samples of appropriate shape and width for transmission of irradiating radiation. Referring now to FIG. 3A, it can be seen that the absorbance 44 for dissolved polycarbonate increases at 320 nm as a function of sample Fries products 48 for dissolved polycarbonate. Preferably, the use of absorbance to monitor Fries products is insensitive to non-Fries species in the sample which fluoresce, absorb, or scatter light. For example, absorbance measurements of linear and branched Fries products in melt polycarbonate are not sensitive to the presence of catalysts or other species which may fluoresce. Referring now to FIG. 3, absorbance measurements 52, 54, 56 and 58 of melt polycarbonate having very similar levels of Fries products are not sensitive to the fact that the melt polycarbonate samples are made using different catalysts. This can be compared to fluorescence measurements 62, 64, 66, and 68 for the same samples, which may vary widely, even for samples comprising very similar amounts of Fries.

Also, the use of absorbance to monitor Fries products is preferably insensitive to the reaction environment and reactor design. The characteristics of melt polycarbonate often vary depending upon the method of synthesis, such that the final product may have very different physical and chemical properties depending upon reaction temperature, type of reactor, and levels of starting materials. For example, the reaction temperature may affect the rate of polymer molecular weight build-up, whereas the reactor type (i.e. batch as opposed to continuous) may affect the rate of polymerization. Also, the levels of starting materials (e.g. bisphenol A and diphenyl carbonate) can affect the characteristics of the polymer product. Referring again to FIG. 3A, it can be seen that absorbance measurements 70 and 72 of polycarbonate having very similar levels of Fries products are not sensitive to the fact that polycarbonate samples are made using two different reactor designs. Conversely, fluorescence measurements 74 and 76 of the same samples are quite different from each other.

Also, the measurement of Fries in polymer samples preferably is not sensitive to variations in polymer molecular weight. For example, melt polycarbonate samples ranging in molecular weight from 2008 to 3154 have absorbance measurements 52, 54, 56 and 58, consistent with a relative narrow range of measured Fries (FIG. 3).

Figure 4:
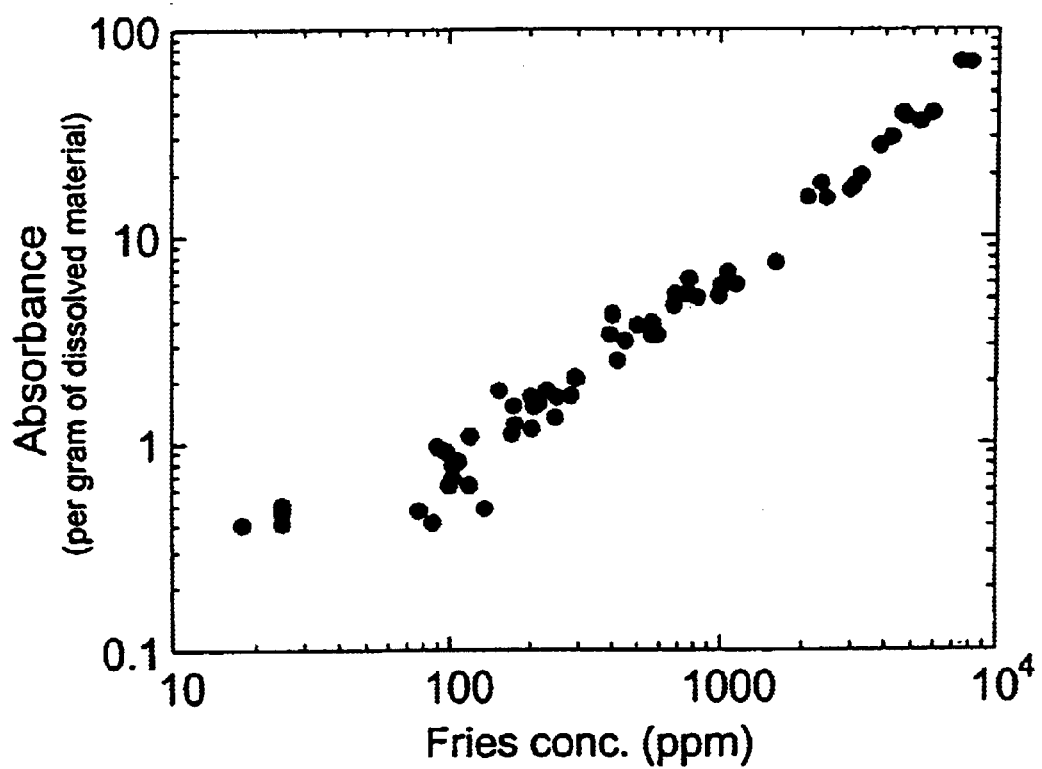
FIG. 4 illustrates an aspect of an embodiment of the invention comprising a plot of absorbance at 320 nm of dissolved oligomer and polymer melt polycarbonate samples made using different catalysts, reactor designs, and final reaction temperatures as a function of Fries concentration.

Thus, in an embodiment, and as summarized in FIG. 4, which shows data for polycarbonate polymers made in several different types of reactors, and using 9 different catalysts at a final temperature of 280° C., or using 5 different catalysts at a final temperature of 310° C., as well as oligomers made in different types of lab scale reactors and using 5 different catalysts, quantification of Fries in polymer samples by the methods of the invention is relatively insensitive to final reaction temperature, catalyst, reactor design, or nature (i.e. oligomer or polymer) of the final product.

Absorbance measurements may be taken at a unique wavelength, as shown in FIGS. 2, 3, and 4, or performed over the entire absorption band. Where the absorbance spectrum comprises several wavelengths or an entire absorption band, the absorbance characteristics of the sample may be determined using multivariate calibration algorithms such as Partial Least Squares Regression (PLS), Principal Components Regression (PCR), and the like (see e.g. Beebe, K. R. et al., Chemometrics: A Practical Guide; Wiley, New York, N.Y., pp, 183–339 (1998)). Given a large enough span of calibration samples, multivariate calibration models are generally more robust than univariate models due to enhanced outlier detection capabilities and increased tolerance toward slight shifting in peak position or band shape. Also, multivariate calibration models allow for measurement of more than one variable or component of interest. PLS models correlate the sources of variation in the spectral data with sources of variation in the sample. Preferably, the PLS model is validated by statistical techniques. Such statistical techniques include, but are not limited to, leave one out cross-validation, venetian blinds, and random subsets (see e.g. Beebe, K. R., et al., Chemometrics: A Practical Guide, Wiley, New York, N.Y. (1998)).

Thus, in an embodiment, the absorption spectrum comprises UV/visible wavelengths. Alternatively, the absorption spectrum may specifically comprise UV wavelengths or visible wavelengths. For analysis of sample Fries, the monitored absorbance preferably comprises at least one monochromatic wavelength in the range of 250 to 450 nm. More preferably, the monitored absorbance comprises at least one monochromatic wavelength in the range of 280 to 400 nm. Even more preferably, the monitored absorbance comprises at least one monochromatic wavelength in the range of 290 to 330 nm. Even more preferably, the monitored absorbance comprises a wavelength of about 320 nm.

In an embodiment, the method is used to measure additional reaction components other than Fries. By multivariate analysis, the presence and/or amount of multiple sample components, such as linear Fries, branched Fries, and phenolic end-groups is determined for each sample. For example, for the analysis of sample Fries and uncapped end-groups, the monitored absorbance preferably comprises at least two monochromatic wavelengths in the range of 250 to 450 nm. More preferably, the monitored absorbance comprises at least two monochromatic wavelengths in the range of 260 to 400 nm. Even more preferably, the monitored absorbance comprises at least two monochromatic wavelengths in the range of 270 to 340 nm.

Multivariate analysis may be used to characterize the amount of linear Fries, branched Fries, or uncapped phenolic end-groups, as well as all three components. For example, and referring now to FIG. 5, PLS can be used to distinguish samples comprising linear Fries 80 and branched Fries 82, from samples which comprise mixtures of linear and branched Fries 84. By comparing the test sample to known controls, the amounts of linear and branched Fries may be delineated (FIGS. 6 and 7, respectively).

Figure 8:
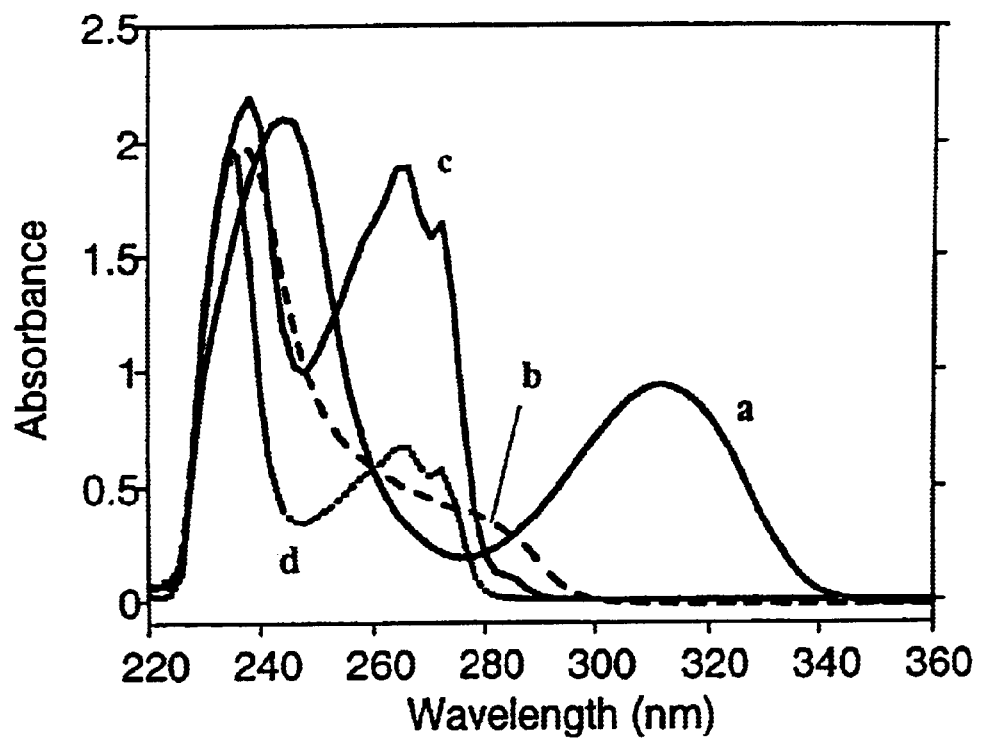
FIG. 8 illustrates an aspect of an embodiment of the invention comprising UV/visible absorbance spectra of samples of pure components comprising (a) entirely linear Fries; (b) branched Fries; (c) polycarbonate with 0% end-capped phenolic end-groups and no Fries; and (d) polycarbonate with 100% end-capped phenolic end-groups and no Fries.

Similarly, multivariate analysis may be used to characterize the amount of linear Fries, branched Fries and uncapped phenolic end-groups. Referring now to FIGS. 8, 9, and 10, spectra from samples comprising known mixtures of linear Fries, branched Fries and phenolic end-groups can be distinguished and used for quantitative determination of each component of interest. FIG. 8 depicts UV/visible absorbance spectra of samples of pure components comprised of entirely of linear Fries (a); branched Fries (b); polycarbonate with 0% end-capped phenolic end-groups and no Fries (c); and polycarbonate with 100% end-capped phenolic end-groups and no Fries (d).

Figure 9A:
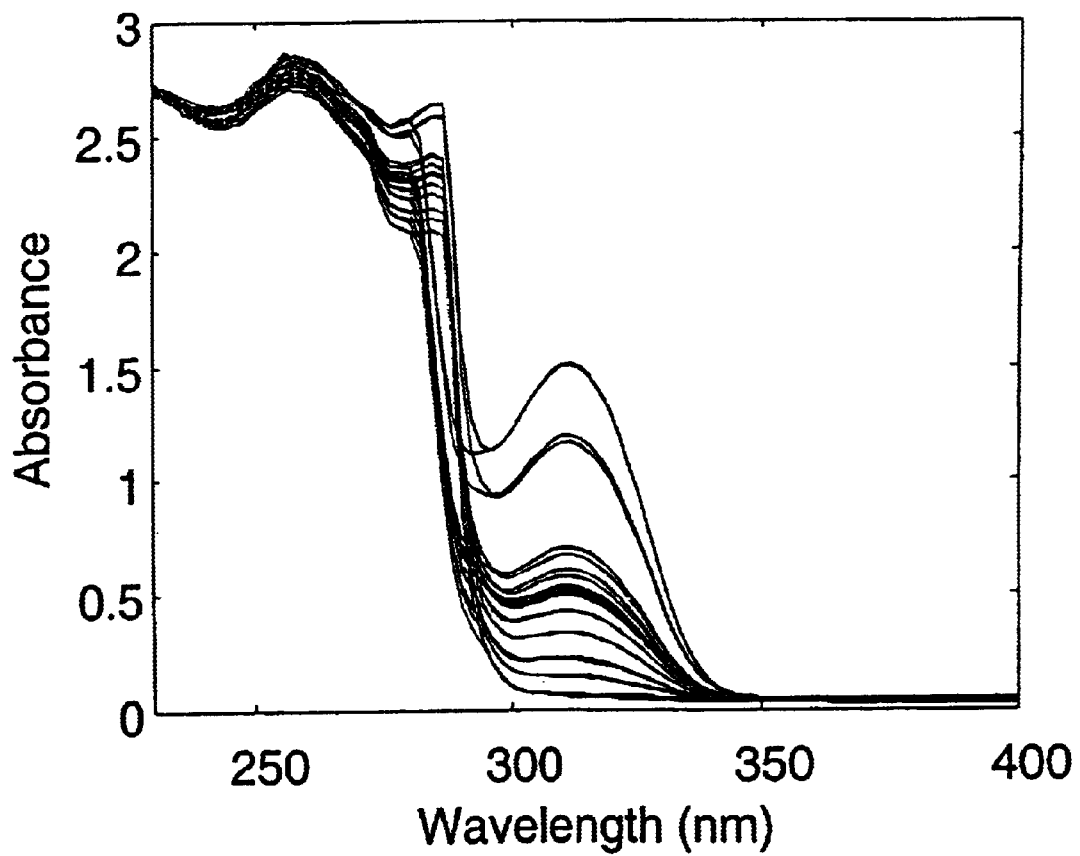
FIG. 9 illustrates an aspect of an embodiment of the invention comprising multivariate determination of linear and branched Fries wherein (A) shows UV/visible absorbance spectra of polycarbonate samples with variable amounts of capped end-groups, phenolic end-groups, linear Fries, and branched Fries; (B) illustrates calibration results of a multivariate PLS model for determination of linear Fries using the spectra shown in (A); and (C) illustrates calibration results of a multivariate PLS model for determination of branched Fries using the spectra shown in (A).
Figure 9B:
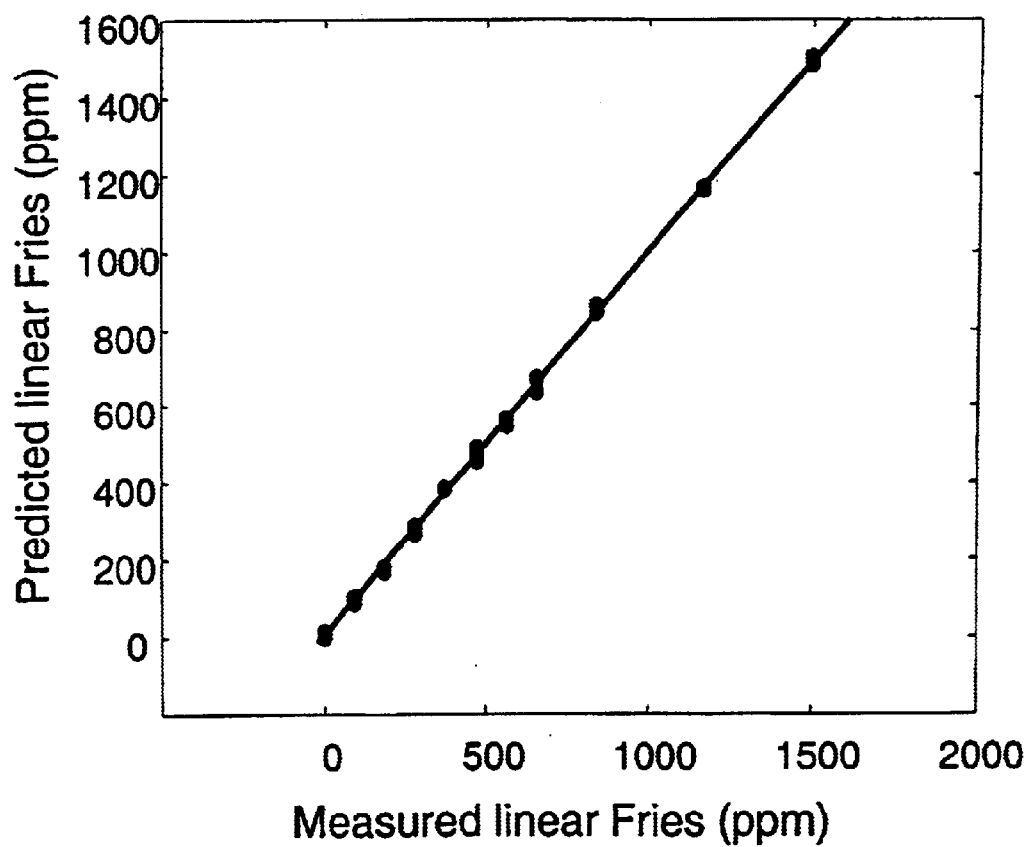
Figure 10A:
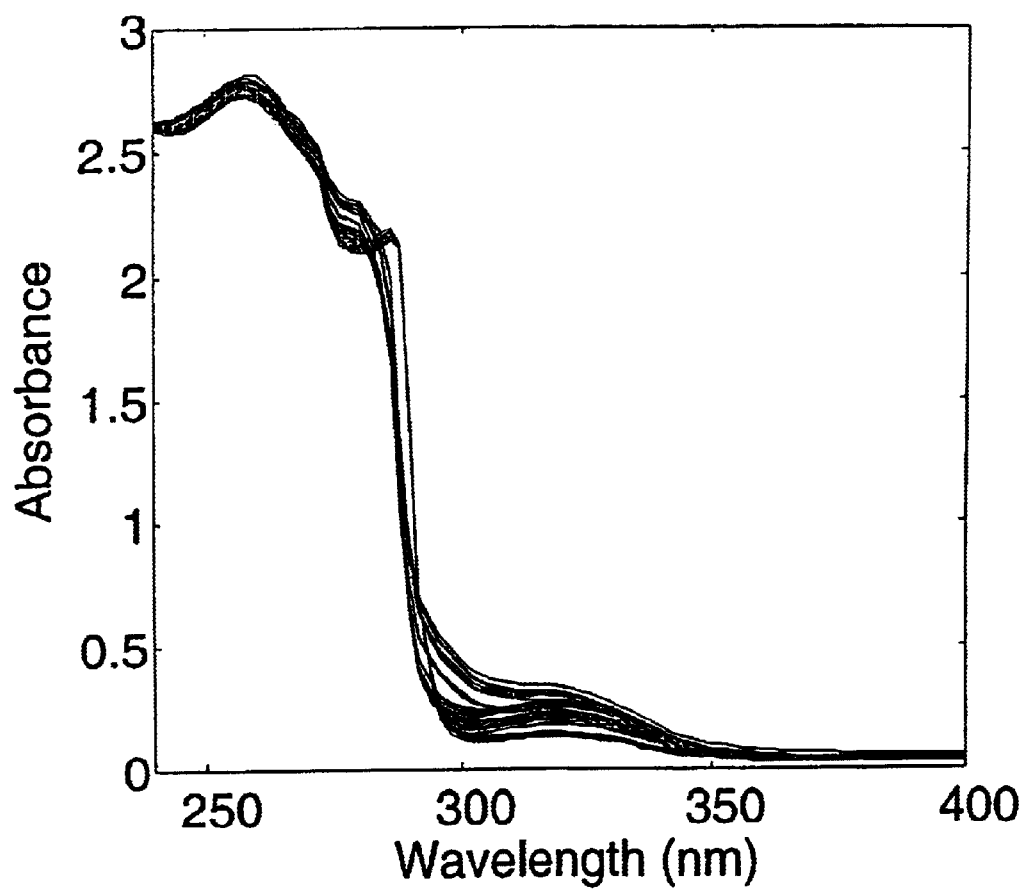
FIG. 10 illustrates an aspect of an embodiment of the invention comprising multivariate determination of linear and branched Fries and phenolic end-groups wherein (A) shows UV/visible absorbance spectra of polycarbonate oligomeric and polymeric samples with variable amounts of phenolic (—OH) end-groups, linear Fries, and branched Fries; (B) illustrates calibration results of a multivariate PLS model for determination of linear Fries using the spectra shown in (A); (C) illustrates calibration results of a multivariate PLS model for determination of branched Fries using the spectra shown in (A); and (D) illustrates calibration results of a multivariate PLS model for determination of phenolic end-groups using the spectra shown in (A).
Figure 10B:
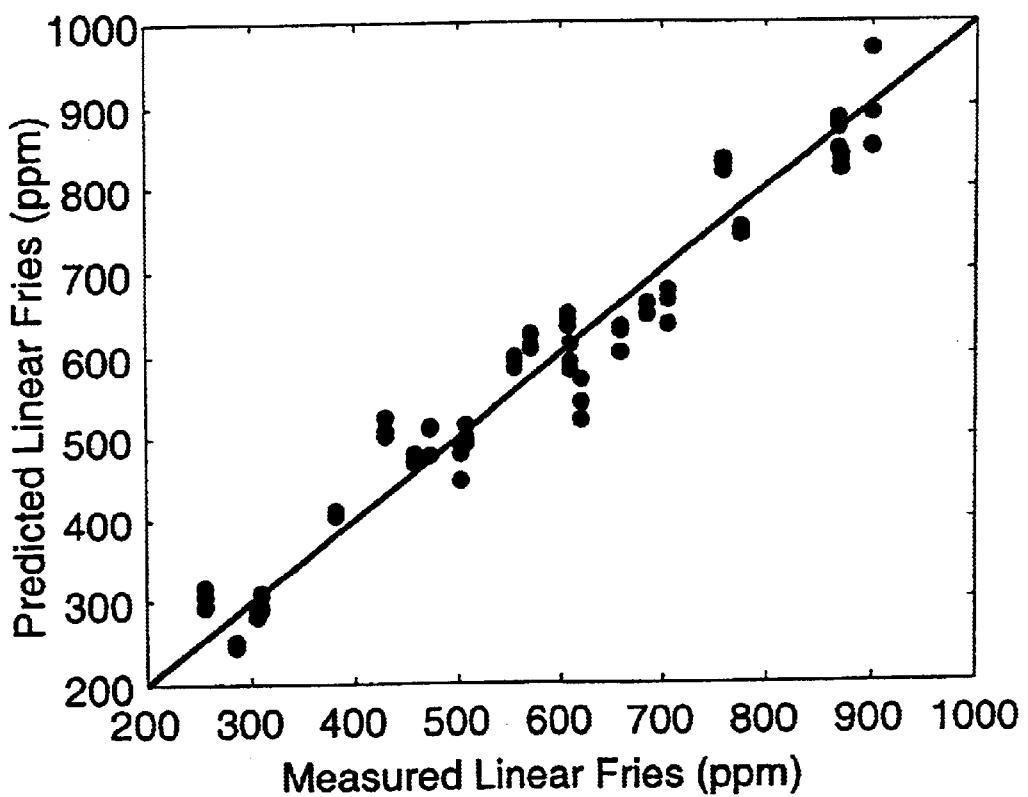
Figure 10C:
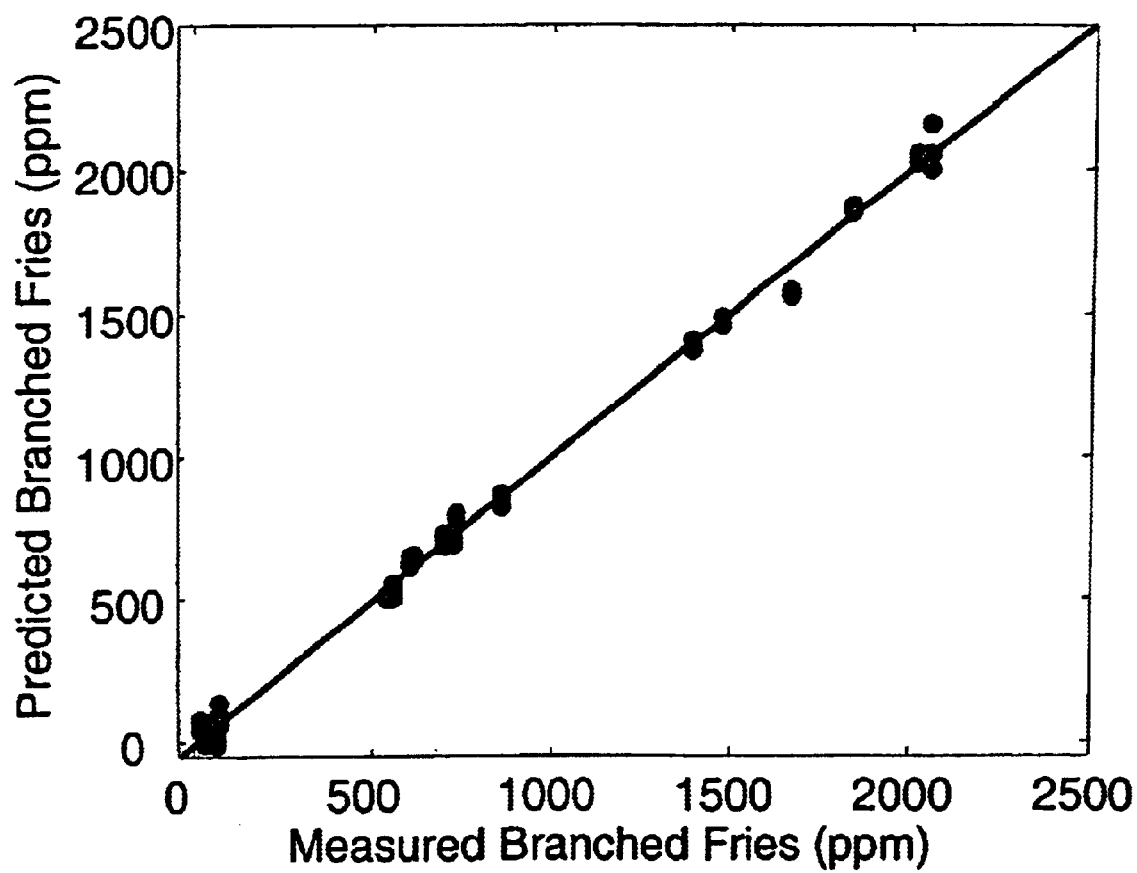
Figure 10D:
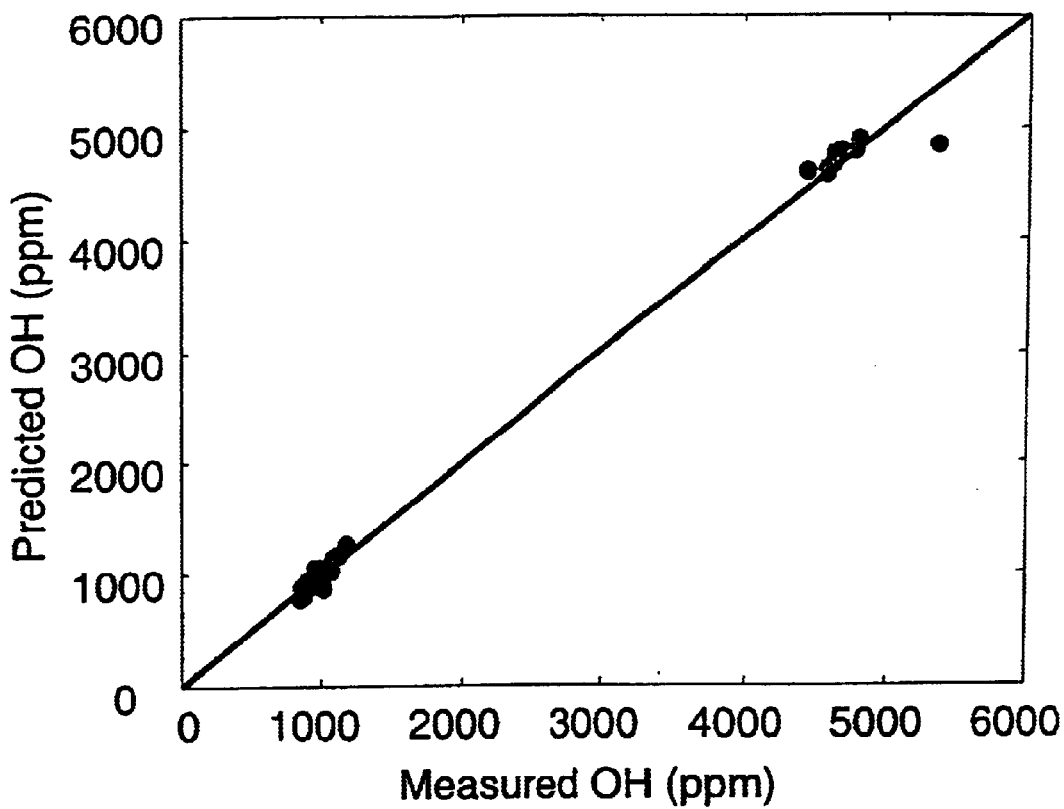

Although samples of pure components may be distinguished visually (FIG. 8), multicomponent mixtures typically require multivariate analysis to distinguish various reaction components. FIG. 9A illustrates UV/visible absorbance spectra of laboratory prepared multicomponent samples comprised of polycarbonate with predetermined amounts of phenolic end-groups, linear Fries, and branched Fries. FIGS. 9B and C illustrate the use of PLS modeling for determination of linear Fries and branched Fries, respectively, from the spectra of FIG. 9A. FIG. 10 illustrates a similar analysis, using polymeric and oligomeric polycarbonate samples made in a production-scale reactor. FIG. 10A illustrates UV/visible absorbance spectra of the samples, 10B and C illustrate the use of PLS modeling for determination of linear Fries and branched Fries from the spectra of 10A, respectively, and 10D illustrates the use of PLS modeling for determination of phenolic (—OH) end-groups from the spectra of 10A. Thus, the invention comprises a method for direct measurement of Fries and uncapped phenolic end-groups in polycarbonate. The polycarbonate may be polymers or oligomers, or a mixture of both. The method operates by determination of Fries concentration and phenolic end-groups from a spectroscopic property such as UV/visible absorbance. Determinations may be performed at a single wavelength or over the entire absorption band. Preferably, the method is used for determination of Fries product in the presence of other fluorescent, absorbing, and scattering species which are not Fries products. When used to assess Fries product formed during melt polymerization, the method is independent of the reaction temperature, polymer molecular weight, reactor design, and the catalyst used for polymerization.

As will be recognized by those of ordinary skill in the art, all or part of the steps in the method of the present invention may be coded or otherwise written in computer software, in a variety of computer languages including, but not limited to, C, C++, Pascal, Fortran, Visual Basic®, Microsoft Excel, MATLAB®, Mathematica®, Java, and the like. Accordingly, additional aspects of the present invention include computer software for performing one or more of the method steps set forth herein. The software code may be compiled and stored in executable form on computer readable media as, for example, computer ROM, floppy disk, optical disk, hard disks, CD ROM, or the like.

For example, an embodiment of a system for performing the methods of the invention comprises melt polycarbonate and a means for transmitting light through a sample of the reaction. Samples are irradiated with excitation light of a predetermined wavelength and absorbance at a specific wavelength or over a series of wavelengths is monitored using a spectrophotometer or other monitoring device. The absorbance profile is than used to predict the amount of Fries products in the sample. The invention may be further understood by reference to the following non-limiting examples.

EXAMPLE 1

The capabilities of absorption detection of Fries product have been experimentally tested on solid polycarbonate resin with varying amount of Fries. For these experiments, a desktop diode array spectrophotometer (Hewlett Packard, Palo Alto, Calif.; Model 8452A) and a fiber-optic spectrometer (Ocean Optics Inc., Dunedin, Fla.; Model ST2000) with a steady-state Xe arc lamp (450-W Xe arc lamp; SLM Instruments, Inc., Urbana, Ill. Model FP-024) was used. The emission level of the Xe arc lamp was attenuated in order not to saturate the spectrometer. An in-line short-pass (400-nm cut-off) filter (Melles Griot, Inc., Irvine, Calif.) was used to block intense radiation above 400 nm. For measurements of Fries over the 01000 ppm range, an optical pathlength of 12 mm is used.

Melt polycarbonate oligomeric samples were produced using either a continuous reactor at a rate of about 2 kg per hour or a small-scale (1 liter) batch reactor as shown in Table 1. Solid polycarbonate samples were 1.64.1 mm thick plaques which varied in thickness over the sample surface by 0.020.2 mm. For example, a pathlength of about 0.5–5 mm, or about 1–2 mm, can be used to measure Fries levels between 0–1,000 ppm, and 0–8,000 ppm, respectively, depending on the analytical wavelength used.

Actual levels of Fries products (in ppm) were measured by liquid chromatography as previously described in U.S. Pat. No. 6,184,334 after methanolysis in potassium hydroxide. Briefly, 0.5 g polycarbonate was dissolved in 4.0 ml of tetrahydrofuran (THF) containing para-terphenyl as an internal standard. Potassium hydroxide (3.0 mL of 18% KOH in methanol) was then added and the resulting mixture stirred for 2 hours at 25° C. and then 1.0 mL acetic acid added and the mixture was stirred for 5 min. After removal of the resultant potassium acetate crystals, the filtrate was analyzed by liquid chromatography. Polymer molecular weight (number average molecular weight: Mn) was measured by gel permeation chromatography (GPC) at 25° C. using chloroform as the mobile phase (U.S. Pat. No. 6,184,334). Standards of polystyrene were used to construct a universal calibration against which polycarbonate could be measured using the Mark-Houwink equation. Terminal structure and the concentration of terminal —OH groups (phenolic endgroups) was obtained as described in U.S. Pat. No. 5,151,491 using $^{13}C$ NMR and IR spectroscopy. Table 1 summarizes the characteristics of the polycarbonate samples used in these experiments.

TABLE 1

Evaluation of Melt Polycarbonate by UV/Visible Absorbance and Fluorescence

| Sample number | Reactor type* | Catalyst | Fries (ppm) | Mn | EC % |
|---|---|---|---|---|---|
| 1 | SS | 1 | 103 | 3154 | |
| 2 | SS | 2 | 103 | 2766 | |
| 3 | SS | 3 | 108 | 2008 | |
| 4 | SS | 4 | 100 | 2356 | |
| 5 | SS | 4 | 175 | 1996 | |
| 6 | SS | 4 | 213 | 2228 | |
| 7 | SS | 4 | 292 | 2715 | |
| 8 | CS | 4 | 250 | 2936 | 54 |
| 9 | CS | 4 | 393 | 2935 | 54 |
| 10 | CS | 4 | 502 | 2789 | 42 |
| 11 | CS | 4 | 687 | 2734 | — |
| 12 | CS | 4 | 770 | 2770 | 37 |
| 13 | SS | 4 | 760 | 3807 | |

*CS = Continuous system; SS = Small Scale system; EC% = percent endcapped groups.
The catalysts used were conventional melt polymerization catalysts as described, for example, in U.S. Pat. Nos. 6,184,334, 6,166,133, and 5,151,491.

Absorbance spectra for solid samples 1–8 (Table 1) were measured using a desktop diode array spectrophotometer (Hewlett Packard Model 8452A). It was found that with increasing amounts of Fries rearrangement products, there is an increase in absorbance at 320 nm. A univariate calibration curve correlating absorbance at 320 nm to known Fries (ppm) is presented in FIG. 2. Shown are error bars which represent one standard deviation (SD) from the mean, where three absorbance spectra were measured for each sample at different locations in the sample.

A similar series of absorbance measurements for samples 1–8 was performed using a portable fiber optic spectrophotometer with a UV light source (Ocean Optics Inc., Dunedin, Fla.; Model ST2000) and a steady state arc lamp (SLM Instruments, Inc., Urbana, Ill.; Model FP-024). Using the portable fiber optic spectrophotometer, the standard deviations for separate determinations using the same samples were similar to that found using the desktop diode array spectrophotometer.

EXAMPLE 2

Shown in FIG. 3 is a comparison of absorbance and fluorescence measurements of Fries using the samples detailed in Table 1. Samples 1–13 (oligomer stage melt polycarbonate) were dissolved in chloroform for measurement of Fries by either absorbance or fluorescence. Absorbance measurements were performed as described above (Example 1). Fluorescence measurements were performed using a white light source (450-W Xe arc lamp, SLM Instruments, Inc.), a monochromator for selection of the excitation wavelength, and a portable spectrofluorometer (Ocean Optics, ST2000). For fluorescence measurements, excitation light from the monochromator was focused into one of the arms of a "six-around-one" bifurcated fiber-optic reflection probe, and emitted light collected by positioning the common end of the fiber-optic probe near the sample at an angle to minimize excitation light reflected from the sample back into the probe. The collected light was transmitted via a second arm of the probe to the spectrofluorometer. The fluorescence channel of the spectrofluorometer was equipped with a 200-$\mu$m slit, 600-grooves/mm grating blazed at 400 nm and covering the spectral range from 250 to 800 nm with efficiency greater than 30%, and a linear CCD-array detector. The intensity of fluorescent emission at 500 nm with excitation at 340 nm was monitored.

A comparison of Fries quantification using absorbance as compared to fluorescence is shown in FIGS. 3A and 3B. It can be seen that fluorescence intensity correlates with absorbance, as expected in a single-species system. In addition, under controlled pathlength and excitation conditions, both fluorescence and absorbance are measured with a precision of 0.2 to 2% RSD. It was found, however, that for single excitation and emission wavelengths, absorbance measurements provide a more accurate estimation of Fries levels than fluorescence. For example, it was found that fluorescence measurements varied dependent upon the type of reactor used for melt polymerization. In the experiment shown in FIG. 3, samples 1–7 and 13 were produced in a small-scale (SS) reactor, whereas samples 8–12 were produced in a continuous reactor system (CS). Although generally fluorescence and absorbance provide accurate predictive values for sample Fries, in some cases (e.g. samples 12 and 13), samples having the same Fries concentration, but produced in different reactors, had very different fluorescence intensity measurements.

It was also found that fluorescence measurements of Fries may vary depending upon the catalysts used in the polymerization reaction. Thus, as seen in FIG. 3, melt polymerization samples 1, 2, 3, and 4 (Table 1) having the same Fries concentration but produced using four different catalysts can have very different fluorescence intensity measurements (i.e. data points 62, 64, 66, and 68 in FIG. 3B). In contrast, absorbance measurements are relatively insensitive to the type of catalyst used to produce the melt polycarbonate (i.e. data points 52, 54, 56, and 58 in FIG. 3A).

Similarly, for samples made in a 1 liter lab reactor, it was found that samples made with different catalysts, but having similar levels of Fries, could have varying levels of fluorescence which did not fall within a univariate model for Fries prediction. The accuracy of univariate models for absorbance and fluorescence was further quantified by three measures: (1) the coefficient of multiple determination $R^2$ which indicates the correlation between predicted and known Fries; (2) the 95% confidence interval (CI) from the regression model; and (3) the 95% prediction interval (PI) from the regression model. Results are presented in Table 2.

TABLE 2

Summary of $R^2$, CI and PI for Univariate Analysis of Data From FIG. 3

|  | Determination of Fries by absorbance | Determination of Fries by fluorescence |
|---|---|---|
| Coefficient of multiple determination ($R^2$) | 99.2% | 91.5% |
| 95% confidence interval (CI), ppm of Fries | 20 | 100 |
| 95% prediction interval (PI), ppm of Fries | 110 | 380 |

EXAMPLE 3

A comprehensive analysis of melt samples collected from different reactor types (i.e. batch and continuous reactor types), two different final reaction temperatures (either 280° C. or 310° C.), different material types (oligomeric and polymeric), and produced with catalysts of different nature was performed. Results are presented in FIG. 4, and include data for polycarbonate polymers made using 9 different catalysts at a final temperature of 280° C. or 5 different catalysts at a final temperature of 310° C., and oligomers made using 5 different catalysts. It can be seen that absorbance of Fries product at 320 nm is correlated with Fries concentration over the investigated concentration range from 0 to 8000 ppm, and that results are generally not sensitive to reactor design, reaction temperature, product size (i.e. oligomer or polymer), or catalyst type.

EXAMPLE 4

Experiments were performed to determine the lower limit of detection of Fries product. The detection limit for monitoring of Fries was defined as the Fries concentration producing a signal three times the standard deviation of the baseline, and was calculated from the slope of the calibration curve over the lowest measured concentration (i.e. about 100 ppm) as described by Ingle and Crouch (J. D. Ingle, Jr., and S. R. Crouch, Spectrochemical Analysis: Prentice Hall: Englewood Cliffs, N.J., 1988, at page 10). Using the data from FIG. 3A, the detection limit by UV analysis was calculated as 0.8–1.5 ppm Fries. Example 5Determinations of linear and branched Fries were performed by preparing solutions of phenyl salicylate, and phenyl carbonate of phenyl salicylate in dichloromethane, that constitute linear and branched Fries moieties, respectively. Samples were prepared that contained linear Fries concentrations ranging from 0 to about 1300 ppm, and branched Fries concentrations ranging from 0 to about 2800 ppm. Additionally, samples of linear and branched Fries mixtures at different ratios and total concentrations were used. UV/visible absorption spectra were measured using a desktop diode array spectrophotometer (Hewlett Packard Model 8452A) as described in Example 1, above. Multivariate spectral analysis was performed using a chemometrics software package PLS_Toolbox (Version 2.0; Eigenvector Research, Inc., Manson, Wash.) operated with MATLAB® software (Version 5.3; The Mathworks Inc., Natick, Mass.).

Figure 5:
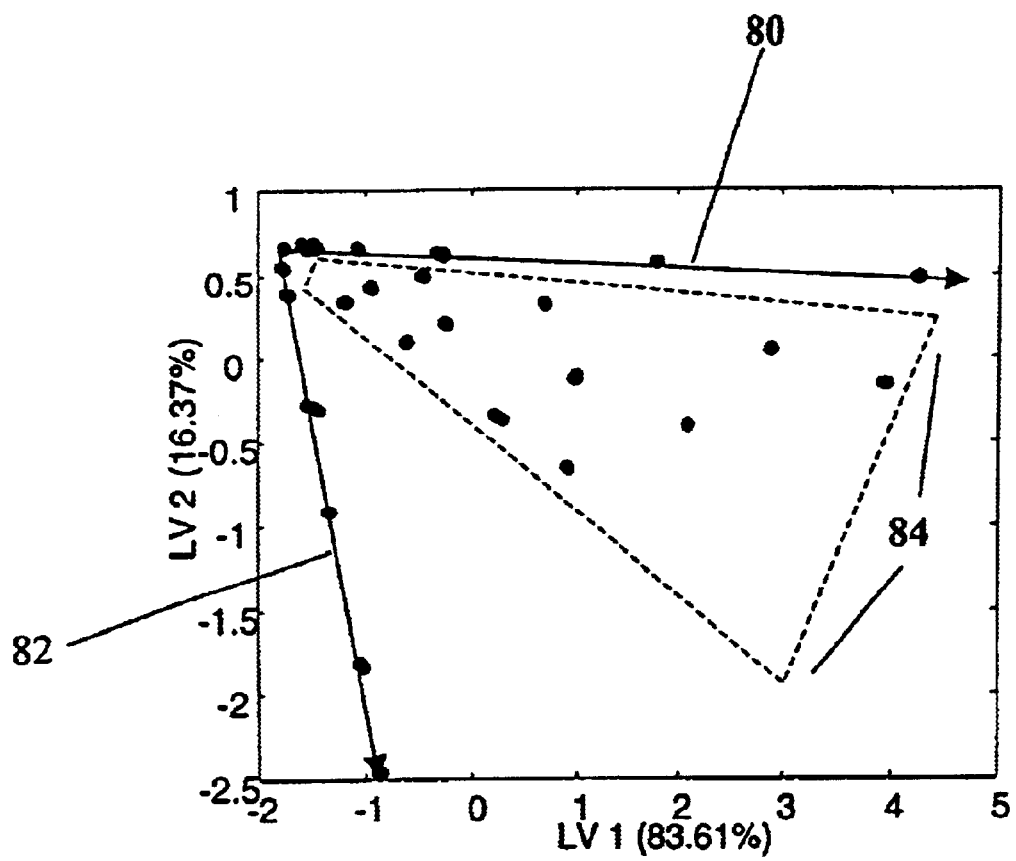
FIG. 5 illustrates an aspect of an embodiment of the invention comprising a scores plot of the first two latent variables of a multivariate PLS model for determination of linear and branched Fries and showing a plot for linear Fries, a plot for branched Fries, and a plot corresponding to mixtures of linear and branched Fries.
Figure 6:
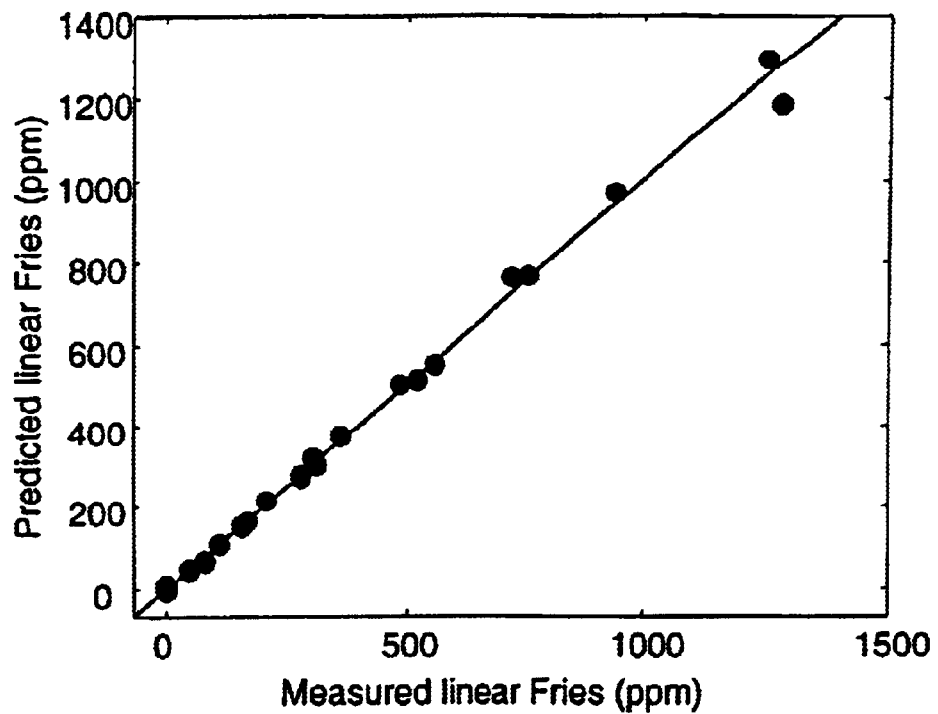
FIG. 6 illustrates an aspect of an embodiment of the invention comprising calibration results of a multivariate PLS model for determination of linear Fries.
Figure 7:
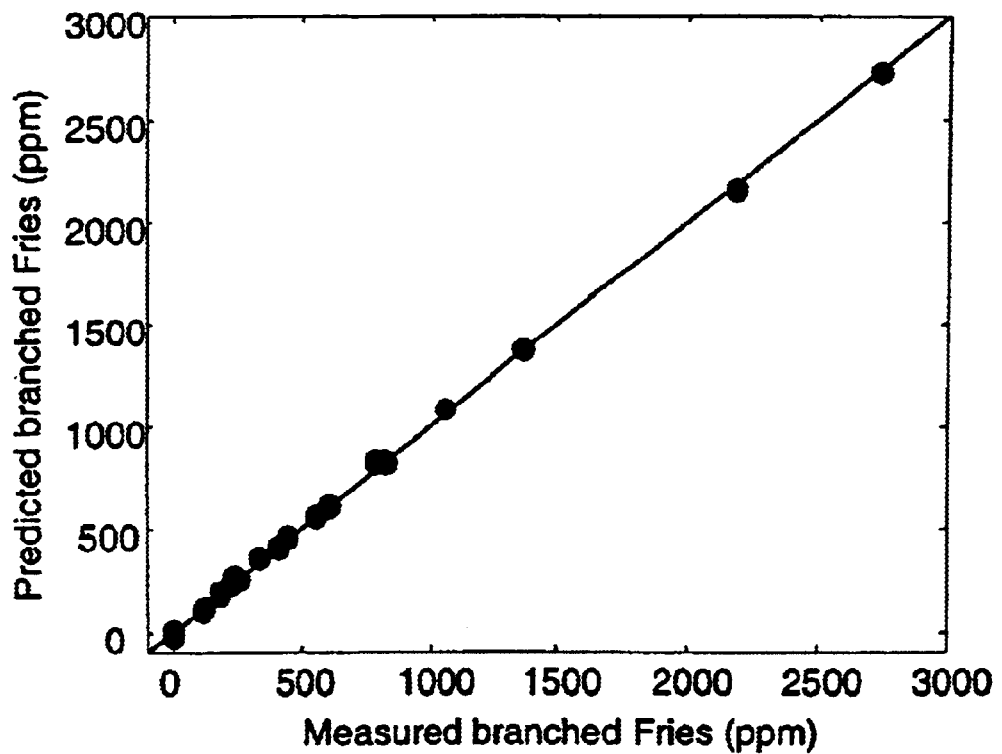
FIG. 7 illustrates an aspect of an embodiment of the invention comprising calibration results of a multivariate PLS model for determination of branched Fries.

FIGS. 5, 6, and 7 illustrate the use of partial least squares (PLS) multivariate analysis to correlate the sources of variation in the spectral data with the changes in concentrations of linear and branched Fries. PLS models were validated using standard methods of leave-one-out is cross-validation (CV) (Beebe, K. R., et al., Chemometrics: A Practical Guide; Wiley, New York, N.Y., 1998) after appropriate preprocessing. In this example, preprocessing consisted of selecting the spectral range for multivariate analysis and mean-centering of the data. FIG. 5 depicts the scores plot of the first two latent variables of a multivariate PLS model for determination of linear and branched Fries where 80 shows the plot for linear Fries; 82 shows the plot for branched Fries; and 84 shows the plot corresponding to mixtures of linear and branched Fries.

Multivariate calibration was used to develop a PLS model for determination of concentrations of linear Fries and branched Fries. Results of a multivariate PLS model for determination of linear Fries and branched Fries are depicted in FIGS. 6 and 7, respectively. The calibration and prediction quality of the multivariate PLS model was estimated using root mean squared calibration (RMSEC) and root mean squared error of cross-validation (RMSECV) for the first two latent variables from the PLS regression model. It was found that a two-factor PLS regression model accounts for more than 95% of the spectral variance and more than 95% of the concentration variance. A summary of the RMSEC and RMSECV for determination of linear Fries and branched Fries in two component samples using UV/visible absorption spectroscopy and multivariate analysis is given in Table 3.

TABLE 3

Determination of Linear and Branched Fries in Two-Component Samples Using UV/Visible Absorption Spectroscopy and Multivariate Analysis

|  | Linear Fries | Branched Fries |
|---|---|---|
| RMSEC[1] | 24 ppm | 17 ppm |
| RMSECV[2] | 26 ppm | 18 ppm |

[1]RMSEC: Root Mean Squared Error of Calibration
[2]RMSECV: Root Mean Squared Error of Cross-Validation

EXAMPLE 6

Determinations of linear and branched Fries and percent end-capped phenolic end-groups were performed by preparing solutions of phenyl salicylate, phenyl carbonate of phenyl salicylate, polycarbonate with 100% of end-capped phenolic end-groups and no Fries, and polycarbonate with 0% of end-capped phenolic end-groups and no Fries in dichloromethane. Phenyl salicylate and phenyl carbonate of phenyl salicylate compounds constitute linear and branched Fries moieties, respectively. Polycarbonate with 100% of end-capped phenolic end-groups and no Fries, and polycarbonate with 0% of end-capped phenolic end-groups and no Fries was prepared by interfacial polymerization.

Samples were prepared that contained mixtures of linear and branched Fries concentrations ranging from 0 to about 1500 ppm, and/or polycarbonate with end-capped phenolic end-groups in the concentration range from 0 to 40%. UV/visible absorption spectra were measured using a desktop diode array spectrophotometer (Hewlett Packard Model 8452A). Multivariate spectral analysis of collected UV/visible spectra was performed using a chemometrics software package PLS_Toolbox (Version 2.0, Eigenvector Research, Inc., Manson, Wash.) operated with MATLAB® software (Version 5.3, The Mathworks Inc., Natick, Mass.)

after appropriate preprocessing of the data. The preprocessing included selection of the spectral range to be used for multivariate analysis, and mean-centering of the data.

FIG. 8 depicts UV/visible absorbance spectra of samples of pure components comprised of: (a) entirely of linear Fries; (b) branched Fries; (c) polycarbonate with 0% end-capped phenolic end-groups and no Fries; and (d) polycarbonate with 100% end-capped phenolic end-groups and no Fries. These spectral features demonstrate that selective determinations of linear Fries, branched Fries, and phenolic end-groups is possible.

Figure 9C:
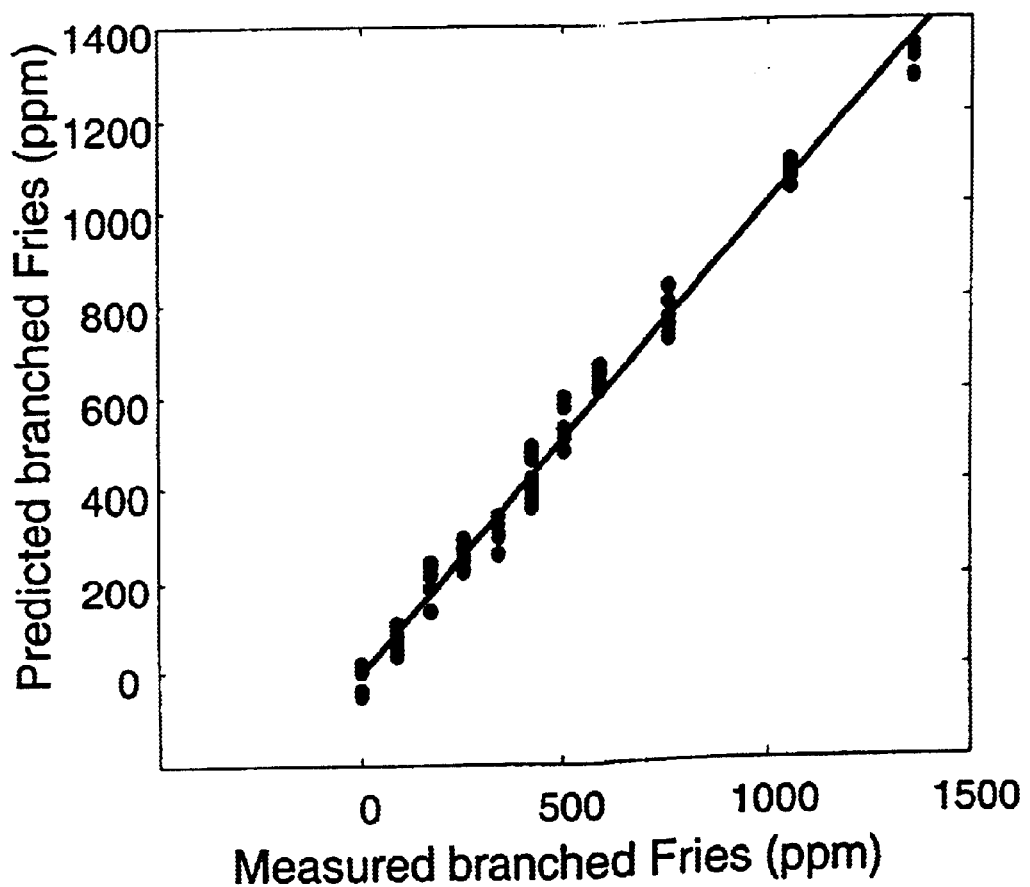

Although samples of pure components may be distinguished visually, multicomponent mixtures typically require multivariate analysis to distinguish various reaction components. FIG. 9A illustrates UV/visible absorbance spectra of prepared multicomponent samples comprised of: polycarbonate with variable amounts of phenolic end-groups, linear Fries, and branched Fries. Calibration results of a multivariate PLS model for determination of linear and branched Fries from the spectra shown in 9A are illustrated in FIGS. 9B and 9C, respectively. The calibration and prediction quality of the multivariate PLS model was estimated by RMSEC and RMSECV using the first four latent variables from the PLS regression model. It was found that a four-factor PLS regression model accounts for more than 95% of the spectral variance and more than 95% of the concentration variance. A summary of the RMSEC and RMSECV values for determination of linear Fries, branched Fries, and phenolic end-groups in multicomponent samples using UV/visible spectroscopy and multivariate analysis is given in Table 4.

TABLE 4

Determination of Linear Fries, Branched Fries, and Phenolic End-Groups is Multicomponent Polycarbonate Samples Using UV/Visible Absorption Spectroscopy And Multivariate Analysis

|  | Linear Fries | Branched Fries | % EC |
| --- | --- | --- | --- |
| RMSEC[1] | 10 ppm | 42 ppm | 0.40% |
| RMSECV[2] | 11 ppm | 46 ppm | 0.45% |

[1]RMSEC = Root Mean Squared Error of Calibration;
[2]RMSECV = Root Mean Squared Error of Cross-Validation.

EXAMPLE 7

Determinations of linear and branched Fries and phenolic end-groups were performed in 22 samples of oligomeric and polymeric polycarbonate materials produced with two different catalysts as described in U.S. Pat. Nos. 6,252,035 and 6,184,334. Independent determinations of total Fries were performed using HPLC (as described for Example 1). Independent determinations of linear Fries, branched Fries, and phenolic end-groups were performed using NMR (as described for Example 1). Using these techniques, it was found that the linear Fries in these samples ranged from about 250 to 870 ppm, branched Fries ranged from 20 to 1940 ppm, and phenolic (—OH) end-groups ranged from about 800 to 5170 ppm.

The samples were dissolved in dichoromethane and their UV/visible absorption spectra were measured using a desktop diode array spectrophotometer (Hewlett Packard Model 8452A) as described in Example 1. Multivariate spectral analysis was performed using a chemometrics software package PLS_Toolbox (Version 2.0; Eigenvector Research, Inc., Manson, Wash.) operated with MATLAB® software (Version 5.3; The Mathworks Inc., Natick, Mass.). PLS models were developed and validated as described in Example 6 after appropriate preprocessing of the data. The preprocessing included selection of the spectral range to be used for multivariate analysis, and mean-centering of the data.

The calibration and prediction quality of the multivariate PLS model was estimated by RMSEC and RMSECV using the first three latent variables from the PLS regression model. It was found that a three factor PLS regression model accounts for more than 95% of the spectral variance and more than 95% of the concentration variance. A summary of the RMSEC and RMSECV values for determination of linear Fries, branched Fries, and phenolic end-groups, in multicomponent oligomeric and polymeric polycarbonate samples using UV/visible spectroscopy and multivariate analysis is given in Table 5.

TABLE 5

Application of UV/Visible Absorption Spectroscopy and Multivariate Analysis for Determination of Linear Fries, Branched Fries, and Phenolic End-Groups in Multicomponent Oligomeric and Polymeric Polycarbonate Samples Prepared Using Two Different Catalysts

|  | Linear Fries | Branched Fries | Phenolic OH end-groups |
| --- | --- | --- | --- |
| RMSEC[1] | 42 ppm | 40 ppm | 130 ppm |
| RMSECV[2] | 45 ppm | 43 ppm | 140 ppm |

[1]RMSEC = Root Mean Squared Error of Calibration;
[2]RMSECV = Root Mean Squared Error of Cross-Validation.

It will be recognized by those in the art that advantages of the spectroscopic method disclosed here over other methods for the on-line, laboratory, and combinatorial screening of Fries products and phenolic end-groups include:

1. ort analysis time providing for rapid assessment of Fries levels;
2. asurement requires minimal or no sample handling or preparation;
3. n-destructive and non-contact analysis in that measurements are performed without destruction of sample or disruption of polymerization process;
4. gh-throughput analysis capable of automation;
5. Sample analysis which is insensitive to fluorescent interferences in the sample;
6. Sample analysis which is insensitive to polymer molecular weight;
7. Sample analysis which is insensitive to reaction temperature;
8. Sample analysis which is insensitive to reactor type; and
9. Operation on small sample size such as that used in combinatorial libraries.

It will be understood that each of the elements described above, or two or more together, may also find utility in applications differing from the types described herein. While the invention has been illustrated and described as embodied in a method for combinatorial or on-line screening, it is not intended to be limited to the details shown, since various modifications and substitutions can be made without departing in any way from the spirit of the present invention. For example, robotic equipment can be used to prepare the samples or modify reaction conditions. Also, various types of parallel analytical screening methods can be incorporated. Also, Fries products derived during reactions other than melt polymerization can be assessed using the techniques described herein. As such, further modifications and equivalents of the invention herein disclosed may occur to persons skilled in the art using no more than routine experimentation, and all such modifications and equivalents are believed to be within the spirit and scope of the invention as defined by the following claims. All patents and publications cited herein are fully incorporated by reference in their entirety.

What is claimed is:

1. A method for monitoring polymer composition comprising:
   irradiating a sample comprising at least one polymer and/or oligomer with at least one substantially monochromatic radiation;
   monitoring UV/visible light absorbed by the irradiated sample; and
   correlating the light absorbed by the irradiated sample to at least one predetermined reaction component, wherein one of the predetermined reaction components comprises Fries rearrangement products.

2. The method of claim 1, wherein the sample comprises polycarbonate.

3. The method of claim 2, wherein the sample comprises melt polycarbonate produced by polymerization of bisphenol A (BPA) and diphenyl carbonate (DPC).

4. The method of claim 1, wherein the Fries rearrangement products comprise linear and branched chain Fries products.

5. The method of claim 1, wherein the Fries rearrangement products consist of linear Fries products.

6. The method of claim 1, wherein the Fries rearrangement products consist of branched Fries products.

7. The method of claim 1, wherein the monitored absorbance comprises at least one substantially monochromatic wavelength in the range of 250 to 450 nm.

8. The method of claim 1, wherein the monitored absorbance comprises at least one substantially monochromatic wavelength in the range of 280 to 400 nm.

9. The method of claim 1, wherein the monitored absorbance comprises at least one substantially monochromatic wavelength in the range of 290 to 330 nm.

10. The method of claim 1, wherein the monitored absorbance comprises a wavelength of about 320 nm.

11. The method of claim 1, further comprising univariate analysis for quantitative prediction of the level of Fries products.

12. The method of claim 1, further comprising monitoring the absorbed light at more than one wavelength.

13. The method of claim 12, further comprising multivariate analysis.

14. The method of claim 1, further comprising correlating the light absorbed by the irradiated sample to a second predetermined reaction component.

15. The method of claim 14, wherein the second predetermined reaction component comprises uncapped phenolic end-groups.

16. The method of claim 15, wherein the monitored absorbance comprises at least two substantially monochromatic wavelengths in the range of 250 to 450 nm.

17. The method of claim 15, wherein the monitored absorbance comprises at least two substantially monochromatic wavelengths in the range of 260 to 400 nm.

18. The method of claim 15, wherein the monitored absorbance comprises at least two substantially monochromatic wavelengths in the range of 270 to 340 nm.

19. The method of claim 1, wherein irradiation and monitoring of absorbed light is performed on solid polycarbonate.

20. The method of claim 1, wherein irradiation and monitoring of absorbed light is performed on dissolved polycarbonate.

21. The method of claim 1, wherein the monitored absorbance is insensitive to the presence of fluorescent species in the sample.

22. The method of claim 1, wherein the monitored absorbance is insensitive to the molecular weight of the sample.

23. The method of claim 1, wherein the monitored absorbance is insensitive to the reaction temperature used to generate the sample.

24. The method of claim 1, wherein the monitored absorbance is insensitive to the reactor type used to generate the sample.

25. Computer readable media comprising software code for performing the method of claim 1.

26. A method for monitoring polycarbonate composition comprising:
   irradiating a polycarbonate sample comprising polymer and/or oligomer with at least two wavelengths of substantially monochromatic radiation;
   monitoring UV/visible light absorbed by the irradiated polycarbonate; and
   correlating the light absorbed by the irradiated polycarbonate to Fries products and un-capped phenolic end-groups in the irradiated polycarbonate.

27. The method of claim 26, wherein the polycarbonate comprises melt polycarbonate produced by polymerization of bisphenol A (BPA) and diphenyl carbonate (DPC).

28. The method of claim 26, wherein the Fries products comprise linear and branched chain Fries products.

29. The method of claim 26, wherein the Fries rearrangement products consist of linear Fries products.

30. The method of claim 26, wherein the Fries rearrangement products consist of branched Fries products.

31. The method of claim 26, wherein the monitored absorbance comprises at least two wavelengths in the range of 250 to 450 nm.

32. The method of claim 26, wherein the monitored absorbance comprises at least two wavelengths in the range of 260 to 400 nm.

33. The method of claim 26, wherein the monitored absorbance comprises at least two wavelengths in the range of 270 to 340 nm.

34. The method of claim 26, wherein the monitored absorbance is insensitive to the presence of fluorescent species in the sample.

35. The method of claim 26, wherein the monitored absorbance is insensitive to the molecular weight of the sample.

36. The method of claim 26, wherein the monitored absorbance is insensitive to the reaction temperature used to generate the sample.

37. The method of claim 26, wherein the monitored absorbance is insensitive to the reactor type used to generate the sample.

38. Computer readable media comprising software code for performing the method of claim 26.

39. A method for monitoring polycarbonate composition comprising:
   irradiating a polycarbonate sample comprising at least one polymer and/or one oligomer with at least one wavelength of substantially monochromatic radiation;
   monitoring UV/visible light transmitted by the irradiated sample; and
   correlating the light absorbed by the irradiated sample to levels of Fries products in the sample.

40. A method for monitoring polycarbonate composition comprising:
   irradiating a polycarbonate sample comprising at least one polymer and/or one oligomer with at least two wavelengths of substantially monochromatic radiation;
   monitoring UV/visible light transmitted by the irradiated sample; and
   correlating the light absorbed by the irradiated sample to levels of linear Fries and branched Fries products in the sample.

41. A method for monitoring polycarbonate composition comprising:

irradiating a polycarbonate sample comprising at least one polymer and/or one oligomer with at least three wavelengths of substantially monochromatic radiation;

monitoring UV/visible light transmitted by the irradiated sample; and correlating the light absorbed by the irradiated polymer to levels of linear Fries and branched Fries products and phenolic end-groups in the sample.

* * * * *